(12) United States Patent
Yoon et al.

(10) Patent No.: US 8,043,613 B2
(45) Date of Patent: Oct. 25, 2011

(54) PODOVIRIEDAE BACTERIOPHAGE HAVING KILLING ACTIVITY SPECIFIC TO STAPHYLOCOCCUS AUREUS

(75) Inventors: Seongjun Yoon, Seoul (KR); Yunjaie Choi, Seoul (KR); Seyung Lee, Pyeongtaek-Si (KR); Jeesoo Son, Seoul (KR); Sooyoun Jun, Seoul (KR); Sanghyeon Kang, Seoul (KR)

(73) Assignee: iNtRON Biotechnology, Inc. (KR)

( * ) Notice: Subject to any disclaimer, the term of this patent is extended or adjusted under 35 U.S.C. 154(b) by 167 days.

(21) Appl. No.: 12/378,457

(22) Filed: Feb. 12, 2009

(65) Prior Publication Data

US 2010/0203019 A1    Aug. 12, 2010

(51) Int. Cl.
*A01N 63/00* (2006.01)
(52) U.S. Cl. .................. 424/93.6; 424/204.1; 424/243.1
(58) Field of Classification Search .................. None
See application file for complete search history.

(56) References Cited

U.S. PATENT DOCUMENTS

| | | | | |
|---|---|---|---|---|
| 6,056,955 | A | 5/2000 | Fischetti | 424/94.1 |
| 6,121,036 | A | 9/2000 | Ghanbari | 436/69.3 |
| 2003/0152594 | A1 | 8/2003 | Pillich | 424/243.1 |
| 2005/0260171 | A1 | 11/2005 | Ghanbari et al. | 424/630 |
| 2010/0203180 | A1 | 8/2010 | Yoon et al. | 514/2 |
| 2010/0254950 | A1 | 10/2010 | Yoon et al. | 424/93.6 |

FOREIGN PATENT DOCUMENTS

| | | |
|---|---|---|
| KR | 2007-82358 | 8/2007 |
| KR | 10-2009-0017862 | 2/2009 |
| KR | 2007-82357 | 2/2009 |
| WO | WO 03/067991 | 8/2003 |
| WO | WO 2004/062677 | 7/2004 |
| WO | WO 2006/063176 | 6/2006 |
| WO | WO 2007/148919 | 12/2007 |
| WO | WO 2009/035303 | 3/2009 |
| WO | WO 2009/035303 | 3/2010 |

OTHER PUBLICATIONS

International Search Report issued Mar. 20, 2009 for WO 2009/035303 published on Mar. 19, 2009 (Application No. PCT/KR2008/005434 filed on Sep. 12, 2008) (Inventors—Yoon et al., Applicant—Intron Biotechnology, Inc.).
Written Opinion issued Mar. 20, 2009 for WO 2009/035303 published on Mar. 19, 2009 (Application No. PCT/KR2008/005434 filed on Sep. 12, 2008) (Inventors—Yoon et al., Applicant—Intron Biotechnology, Inc.).
International Preliminary Report on Patentability issued Mar. 16, 2010 for WO 2009/035303 published on Mar. 19, 2009 (Application No. PCT/KR2008/005434 filed on Sep. 12, 2008) (Inventors—Yoon et al., Applicant—Intron Biotechnology, Inc.).
Accession No: KACC 9700IP, *Staphloccal bacteriophage*, 2007.
Accession No: KCTC 11152BP, *Escherichia coli* pBAD;;Lysin, 2007.
Accession No: KCTC 11151BP, pBAD-TOPO-SALI, 2007.
Accession No: KCTC 11153BP, SAP1 bacteriophage, 2007.
Accession No: KCTC 11154BP, SAP2 bacteriophage, 2007.
Arciola CR, Baldassarri L, Montanaro L, (2001) Presence of IcaA and IcaD genes and slime production in a collection of staphylococcal strains from catheter-associated infections, J. Clin Microbiol. 39(6):2151-2156.
Arciola CR, Montanaro L, Baldassarri L, Borsetti E, Cavedagna D, Donati E, (1999) Slime production by Staphylococcal isolated from prosthesis-associated infections, New Microbiol. 22(4):337-341.
Cisani G, Varaldo PE, Grazi G, Soro O, (1982) High-level potentiation of lysostaphin anti-staphylococcal activity by lysozyme, Antimicrob Agents Chemother. 21(4):531-535.
Costerton JW, Lewandowski Z, DeBeer D, Caldwell D, Korber D, James G, (1994) Biofilms, the customized microniche, J Bacteriol, 176(8):2137-2142.
Cramton SE, Gerke C, Schnell NF, Nichols WW, Götz F, (1999) The intercellular adhesion (ica) locus is present in *Staphylococcus aureus* and is required for biofilm formation, Infect Immun, 67(10):5424-5433.
Graham S, Coote PJ, (2007) Potent, synergistic inhibition of *Staphylococcus aureus* upon exposure to a combination of the endopeptidase lysostaphin and the cationic peptide ranalexin. J Antimicrob Chemother, 59(4):759-762.
Gründling A, Missiakas DM, Schneewind O, (2006) *Staphylococcus aureus* mutants with increased lysostaphin resistance, J Bacteriol, 188(17): 6286-6297.
Kusoma C, Jadanova A, Chanturiya T, Kobai-Kun JF, (2007) Lysostaphin-resistant variants of *Staphylococcus aureus* demonstrate reduced fitness in vitro and in vivo. Antimicrob Agents Chemother. 51(2): 475-482.
Mah TF, O'Toole GA, (2001) Mechanisms of biofilm resistance to antimicrobial agents, Trends Microbiol, 9(1): 34-39.
McKenney D, Pouliot KL, Wang Y, Murthy V, Ulrich M, Döring G, Lee JC, Goldmann DA, Pier GB, (1999) Broadly protective vaccine for *Staphylococcus aureus* based on an in vivo-expressed antigen, 284(5419): 1523-1527.
O'Gara JP, Humphreys H. (2001) *Staphylococcus epidermidis* biofilms; importance and implications, J Med Microbiol, 50(7): 582-587.
Resch A, Fehrenbacher B, Eisele K, Schaller M, Götz F, (2005) Phage release from biofilm and planktonic *Staphylococcus aureus* cells. FEMS Microbiol Lett. 252(1): 89-96.
Sass P, Bierbaum G, (2007) Lytic activity of recombinant bacteriophage phi11 and phi12 endolysins on whole cells and biofilms of *Staphylococcus aureus*, Appl Environ Microbiol, 73(1): 347-352.
Schuch R, Nelson D, Fischetti VA, (2002) A bacteriolytic agent that detects and kills Bacillus anthracis, Nature, 418(6900): 884-889.

(Continued)

*Primary Examiner* — Jennifer Graser
(74) *Attorney, Agent, or Firm* — Ballard Spahr LLP

(57) ABSTRACT

The present invention relates to a novel bacteriophage, more precisely a Podoviridae bacteriophage having killing activity specific to *Staphylococcus aureus* which is the causing agent of infectious disease in human and animals, a pharmaceutical composition for the prevention and treatment of the disease caused by *Staphylococcus aureus*, an antibiotic and a disinfectant containing the bacteriophage as an active ingredient.

10 Claims, 4 Drawing Sheets

OTHER PUBLICATIONS

Severance PJ, Kauffman CA, Sheagren JN, (1980) Rapid identification of *Staphylococcus aureus* by using lysostaphin sensitivity, J Clin Microbiol, 11(6): 724-727.

Vybiral D, Takác M, Loessner M, Witte A, von Absen U, Bläsi U. (2003) Complete nucleotide sequence and molecular characterization of two lytic *Staphylococcus aureus* phages: 44AHJD and P68, FEMS Microbiol Lett, 219(2): 275-283.

Waldvogel FA, (2000) Infections Associated with Indwelling Medical Devices, pp. 55-88, 2000, ASM, Washington, DC.

Preliminary Amendment filed Mar. 12, 2010 for U.S. Patent Application Publication No. 2010/025495 (U.S. Appl. No. 12/677,990 filed on Mar. 12, 2010) (Inventors—Yoon et al.).

Walencka E, Sadowska B, Rózalska S, Hryniewicz W, Rózalska B, (2006) *Staphylococcus aureus* biofilm as a target for single or repeated doses of oxacillin, vancomycin, linezolid and/or lysostaphin, Folia Microbiol (Praha), 51(5): 381-386.

Wu JA, Kusuma C, Mond JJ, Kokai-Kun JF, (2003) Lysostaphin disrupts *Staphylococcus aureus* and *Staphylococcus epidermidis* biofilms on artificial surfaces, Antimicrob Agents Chemother, 47(11): 3407-3414.

PODOVIRIEDAE BACTERIOPHAGE HAVING KILLING ACTIVITY SPECIFIC TO STAPHYLOCOCCUS AUREUS

TECHNICAL FIELD

The present invention relates to a novel Podoviridae bacteriophage having killing activity specific to *Staphylococcus aureus*.

BACKGROUND ART

Bacteriophage is a kind of virus-like microorganism infecting bacteria and generally called 'phage' in short. Bacteriophage is an organism having a simple structure wherein a central genetic material composed of nucleic acid is covered by a protein envelope. The nucleic acid is single stranded or double stranded DNA or RNA. To survive, bacteriophage needs a host bacterium and every bacterium has a specific partner bacteriophage. When bacteriophage invades into a host bacterium, it multiplicates itself and then induces expressions of enzymes involved in the decomposition of cell wall of the host bacterium. The enzymes destroy cell wall by attacking the peptidoglycan layer which is responsible for rigidity and mechanical strength of cell wall.

Bacteriophage was first found by Twort, an English bacteriologist, in 1915 during his research on the phenomenon that micrococcus colony is decomposed turning transparent by something. And in 1917, a French bacteriologist d'Herelle found out that there was something that decomposes *Shigella disentriae* in filtrate of feces of a patient with dysentery, and he continued to study to identify the material, leading to the finding of bacteriophage which means "eating bacteria". Since then, bacteriophages against *Shigella dysenteriae, Salmonella typhi*, and *Vibrio cholerae* were further identified. Since penicillin was found by Flemming in 1950, antibiotics have been widely used and the study on bacteriophage continued only in some East European countries and it became out of concern in many other countries. However, since 2000, multidrug-resistant pathogenic bacteria resulted from over-use and/or mis-use of antibiotics have been frequently reported. Because of potential as an alternative for the conventional antibiotics, bacteriophage became in the spotlight again and the studies on bacteriophage are actively undergoing led by advanced countries.

Even though antibiotics (or antibacterial agents) are still major therapeutic agents for the treatment of various infectious diseases, it has been a serious problem since 1980s that the excessive use of such antibiotics generates numbers of multi-drug resistant strains. In 1986, *Staphylococcus aureus* having resistance against vancomycin, which is so called 'the drug of last resort', and other multi-drug resistant strains were found, giving a great shock to those in medical field. Vancomycin resistant enterococci (VRE) were first reported in France in 1986 and first separated in USA in 1988. Since then, the cases of VRE infection have been increased every year with high frequency, everywhere including Europe, USA, Singapore, Japan, Australia, Korea, etc, making the VRE as a causal agent of nosocomial infections. In Korea, VRE was first isolated in 1992. As for *Staphylococcus aureus*, vancomycin-resistant *Staphylococcus aureus* (VRSA) was first found in the early 1990s and was first found in Korea in June, 1996.

Therefore, it is an urgent request to develop a novel antibiotic to treat the infectious diseases caused by bacteria resistant against conventional antibiotics and further to lead national health and medical techniques. Again, it is urgently required to develop an alternative antibiotic to solve the problems of multi-drug resistant bacteria along with the abuse or misuse of the conventional antibiotics and the bio-accumulation of antibiotics. To solve the problem of such resistant bacteria, an alternative antibiotic has to be developed by a completely and fundamentally different method.

In the previous study, the present inventors isolated a Myoviridae bacteriophage capable of killing specifically *Staphylococcus aureus*, and deposited the bacteriophage at Korean Agricultural Culture Collection, National Institute of Agricultural Biotechnology on Jun. 14, 2006 (Accession No: KACC 97001P) and at Biological Resource Center, Korea Research Institute of Bioscience and Biotechnology on Jul. 18, 2007 (Accession No: KCTC 11153BP). The related matters have been applied for a patent (Korean Patent Application No. 2006-55461). Based on the experiences of the present inventors, it can be said that each bacteriophage works on different strains of *Staphylococcus aureus*, precisely every bacteriophage demonstrates bacteriolytic activity against different strains of *Staphylococcus aureus* and shows different spectrums by different mechanisms. Therefore, it is preferred to obtain as diverse bacteriophages as possible. Identifying additional bacteriophage facilitates establishing a method to cope with larger spectrum of *Staphylococcus aureus* and bacteriophage cocktail containing several bacteriophages is expected to have broadened bacteriolytic activity, compared with single kind of bacteriophage.

Technical Problem

Thus, the present inventors first isolated *Staphylococcus aureus* and separated bacteriophage that is able to kill selectively the isolated *Staphylococcus aureus* from the natural system. Then, the inventors investigated the morphological and genetic characteristics of the separated bacteriophage to provide the gene sequence of this genome to distinguish it from other bacterophages. The present inventors finally completed this invention by confirming that the *Staphylococcus aureus* specific bacteriophage isolated by the inventors can be effectively used for the prevention and treatment of the disease caused by *Staphylococcus aureus*.

It is an object of the present invention to provide a novel bacteriophage that is able to selectively kill *Staphylococcus aureus*, the causing agent of infectious disease in animals including human.

It is another object of the present invention to provide a pharmaceutical composition for the prevention and treatment for the disease caused by *Staphylococcus aureus* containing the bacteriophage as an active ingredient.

It is a further object of the present invention to provide an antibiotic containing the bacteriophage as an active ingredient.

It is also an object of the present invention to provide a disinfectant containing the bacteriophage as an active ingredient.

Technical Solution

The present invention provides a bacteriophage belonging to φ29-like virus genus, Podoviridae family, which has killing activity specific to *Staphylococcus aureus*.

The bacteriophage of the present invention has the genome comprising the nucleotide sequence represented by SEQ. ID. NO: 1

*Staphylococcus aureus* is a causing agent of skin infection and food poisoning. It is a very dangerous pathogenic bacterium having strong resistance against methicillin as high as 73% at average, which is the top level among all the antibiotic resistant bacteria in the world. That means 73% of *Staphylococcus aureus* cannot be killed by the antibiotics, which means this bacterium is highly antibiotic resistant.

The present inventors have been studied to kill *Staphylococcus aureus* selectively. The inventors isolated *Staphylococcus aureus* from pathogen and a novel Podoviridae bacteriophage that is able to kill the isolated *Staphylococcus aureus* selectively. This novel bacteriophage having killing activity specific to *Staphylococcus aureus*, separated by the inventors, was named 'SAP-2' and deposited at Korean Collection for Type Cultures, Korea Research Institute of Bioscience and Biotechnology on Jul. 18, 2007 (Accession No: KCTC 11154BP).

The present invention provides a nucleic acid sequence of the genome of bacteriophage SAP-2 selected by the present inventors.

In this invention, the term 'nucleic acid' indicates DNA (gDNA and cDNA) and RNA in a large sense. Nucleotide, the basic unit of nucleic acid, can be not only natural nucleotide but also its analogue having modified sugar or base (Scheit, *Nucleotide Analogs*, John Wiley, New York (1980); Uhlman and Peyman, *Chemical Reviews*, 90:543-584(1990)).

The present invention also provides a pharmaceutical composition for the prevention and treatment of a disease caused by *Staphylococcus aureus* containing the bacteriophage SAP-2 as an active ingredient.

The bacteriophage included in the pharmaceutical composition of the present invention can kill *Staphylococcus aureus* specifically, so that it is very effective in the treatment of various diseases caused by *Staphylococcus aureus*.

*Staphylococcus aureus* is the number one reason to cause infectious mastitis in cattle. *Staphylococcus aureus* is found in 90% of the total dairy cows in USA and 10% of the total dairy cows are presumably infected by this pathogenic bacterium. *Staphylococcus aureus* is a causing agent of acute dermatitis in human, and this acute dermatitis can be suddenly developed into sepsis taking a patient's life. *Staphylococcus aureus* is also a causing agent of pyogenic disease, sweat odor and food poisoning.

Thus, the pharmaceutical composition of the present invention can be used for the treatment of various diseases caused by *Staphylococcus aureus* such as mastitis, acute dermatitis, sepsis, pyogenic disease, food poisoning, pneumonia, osteomyelitis, impetigo, bacteremia, endocarditis and enteritis. According to a preferred embodiment of the present invention, every day spray of the bacteriophage of the invention on the lesion of dairy cow having mastitis could significantly reduce the symptoms of mastitis, suggesting that the bacteriophage of the invention is effective in the treatment of mastitis.

The term 'treatment' herein indicates (i) the prevention of the disease caused by *Staphylococcus aureus*; (ii) the inhibition of the disease caused by *Staphylococcus aureus*; and (iii) the relief of the disease caused by *Staphylococcus aureus*.

The pharmaceutical composition of the present invention can additionally include a pharmaceutically acceptable carrier, which is exemplified by lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but not always limited thereto. The pharmaceutical composition of the present invention can also include a lubricant, a wetting agent, a sweetener, a flavor, an emulsifier, a suspending agent, and a preservative, in addition to the above ingredients.

The pharmaceutical composition of the present invention can be applied or sprayed on the lesion, and administered orally or parenterally (for example, intravenous, intramuscular, hypodermic, local or peritoneal injection).

The effective dosage of the pharmaceutical composition of the present invention varies from the formulation, administration pathway, age, weight, gender, severity of a disease, diet, administration frequency and pathway, excretion and sensitivity. In general, the dosage can be determined by an experienced doctor with consideration of the goal of the treatment or preventive effect. In this invention, the pharmaceutical composition contains bacteriophage at the concentration of $1 \times 10^3$-$1 \times 10^{10}$ pfu/ml, and more preferably $1 \times 10^6$-$1 \times 10^9$ pfu/ml.

The pharmaceutical composition of the present invention can be formulated as a unit dose medicine or as a medicine in multidose vehicle by mixing with a pharmaceutically acceptable carrier and/or excipient by the method well known to those in the art. The pharmaceutical formulation can be selected from a group consisting of ointments, solutions, suspensions or emulsions, extracts, powders, granules, tablets or capsules and additionally includes a dispersing agent or a stabilizing agent.

In another preferred embodiment of the present invention, the present invention provides an antibiotic containing the bacteriophage SAP-2 as an active ingredient.

The term 'antibiotic' is used herein as a general term for antiseptics, bactericidal agents and antibacterial agents.

*Staphylococcus aureus* is frequently found in cosmetics along with *Bacillus subtilis*, *E. coli* and *Pseudomonas aeruginosa*. Cosmetics use oil or water as a major ingredient, to which glycerin and sorbitol, which are carbon sources of a microorganism, and amino acid derivatives and a protein which are nitrogen sources of a microorganism, are added, suggesting that there are enough nutrition and ingredients to attract microorganisms including bacteria. In addition, the term of use of the cosmetics is comparatively long, indicating that it is in high risk of contamination by a microorganism. To prevent color changes or odor changes caused by the contamination of a microorganism, an antibacterial agent is necessarily added to cosmetics for a long shelf-life.

A synthetic antiseptic such as parabens is widely used as an additive for cosmetics, but it is potentially dangerous. Particularly, since its accumulation in breast cancer cells was detected, it has been recognized that the accumulation of such synthetic antiseptic via cosmetics might be very harmful. The American Academy of Dermatology's Committee acclaimed the synthetic antiseptic as the number two allergen causing skin trouble. Recently what worries us is that cosmetics for children also include such artificial synthetic antiseptic, suggesting that children are exposed on such harmful antiseptic longer and much, raising the risk seriously. Therefore, it is sincerely requested to develop a natural antiseptic.

The bacteriophage SAP-2 of the present invention is characterized by its high specificity to *Staphylococcus aureus*, compared with other conventional antibiotics. That is, the bacteriophage SAP-2 can selectively kill *Staphylococcus aureus* only without killing useful bacteria, suggesting that it is a highly valuable antibiotic that has less side effects. The bacteriophage-based antibiotics, unlike the conventional antibiotics, do not induce resistance so that their life cycles are comparatively long. Most conventional antibiotics are gradually limited in use because of the increasing resistance. On the other hand, the antibiotic containing the bacteriophage SAP-2 of the present invention as an active ingredient can solve the problem of the antibiotic-resistance and thus has longer life cycling. Therefore, the antibiotic containing the bacteriophage SAP-2 of the present invention as an active ingredient that is able to kill *Staphylococcus aureus* selectively can be effectively used as a novel antibiotic with excellent antibacterial, bactericidal and antiseptic effects. The term 'antibiotic' is used herein as a general term for antiseptics, bactericidal agents and antibacterial agents.

In another preferred embodiment of the present invention, the invention provides a disinfectant containing the bacteriophage SAP-2 as an active ingredient.

The distribution of bacteria separated from nosocomial infection has been changed over the time. According to NNIS (National Nosocomial Infection Surveillance System), USA, Gram-positive bacteria particularly *Staphylococcus aureus* has been increasing in number among those separated bacteria since late 1980s, and this phenomenon is consistent with that in Korea. According to a report made in Korea in 1985, the dominant distribution is *E. coli*, and *Pseudomonas aeruginosa*, coagulase negative *Staphylococcus* and *Staphylococcus aureus* follows in that order. But, the separation of *Staphylococcus aureus* is increasing gradually. Korean Society for Nosocomial Infection Control (KSNIC) reported in 1996 that *Staphylococcus aureus* took 17.2% of total isolated pathogenic microorganisms and *Pseudomonas aeruginosa* (13.8%) and *E. coli* (12.3%) followed. And, 78.8% of the total *Staphylococcus aureus* separated were confirmed to have resistance against antibiotics.

Based on the above finding, the disinfectant containing the bacteriophage SAP-2 of the present invention that is able to kill specifically *Staphylococcus aureus* can be effectively used as a disinfectant specifically for hospitals and public health. It is also available as a general life disinfectant, a food and kitchen disinfectant, and a stall disinfectant.

Advantageous Effect

As explained hereinbefore, the present invention provides a Podoviridae bacteriophage that is able to kill specifically *Staphylococcus aureus*, a pathogenic microorganism. The bacteriophage of the present invention can be effectively used in a variety of fields as a preventive/therapeutic agent for infectious disease caused by *Staphylococcus aureus*, as an antibiotic, as a antibacterial agent for cosmetics, as a natural antiseptic, and as a multi-purpose disinfectant.

DESCRIPTION OF DRAWINGS

The application of the preferred embodiments of the present invention is best understood with reference to the accompanying drawings, wherein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of *Staphylococcus aureus* and Bacteriophage Having Killing Activity Specific to *Staphylococcus aureus*

<1-1> Isolation of *Staphylococcus aureus*

Bacteriophage generally lives together with bacteria in natural system. To separate the bacteriophage specifically infecting *Staphylococcus aureus*, samples were collected from everywhere where the inventors expected *Staphylococcus aureus* lives. To investigate the samples where *Staphylococcus aureus* really exists, the Baird-Parker agar medium, a *Staphylococcus aureus* selection medium, was used.

Particularly, the present inventors selected dairy cow mastitis as a target disease to isolate *Staphylococcus aureus*, the target microorganism. Mastitis is one of the most representative diseases caused by *Staphylococcus aureus*. A sample was taken from milk of a dairy cow with mastitis and *Staphylococcus aureus* was isolated therefrom using the Baird-Parker agar medium, a *Staphylococcus aureus* selection medium. The isolated *Staphylococcus aureus* was identified as *Staphylococcus aureus* by biochemical analysis including Gram staining method, catalase test and analysis with Vitek of bioMeriuex. The results are shown in Table 1.

TABLE 1

| Vitek ID | 200000-0 (A1-18) catalase + Coagulase + |
| --- | --- |
| Type | Gram positive identification card (GPI) |
| Condition | Final |
| Time | 5 hours |
| Organism | *Staphylococcus aureus* |

PB + BAC − OPT + HCS + 6NC + 10B + 40B − ESC − ARG − URE − TZR + NOV − DEX + LAC + MAN + RAF − SAL − SOR − SUC + TRE + ARA − PYR + PUL − INU − MEL − MLZ − CEL − RIB − XYL − CAT + BH/CO +

<1-2> Isolation of the *Staphylococcus aureus* Specific Bacteriophage

To isolate the *Staphylococcus aureus* specific bacteriophage, samples expected to contain the bacteriophage were cultured together with *Staphylococcus aureus*. The culture broth was centrifuged, filtered and then cultured again with *Staphylococcus aureus*, the bait for the isolation of the bacteriophage, and then lysis of *Staphylococcus aureus* was investigated by plaque assay.

Figure 1:
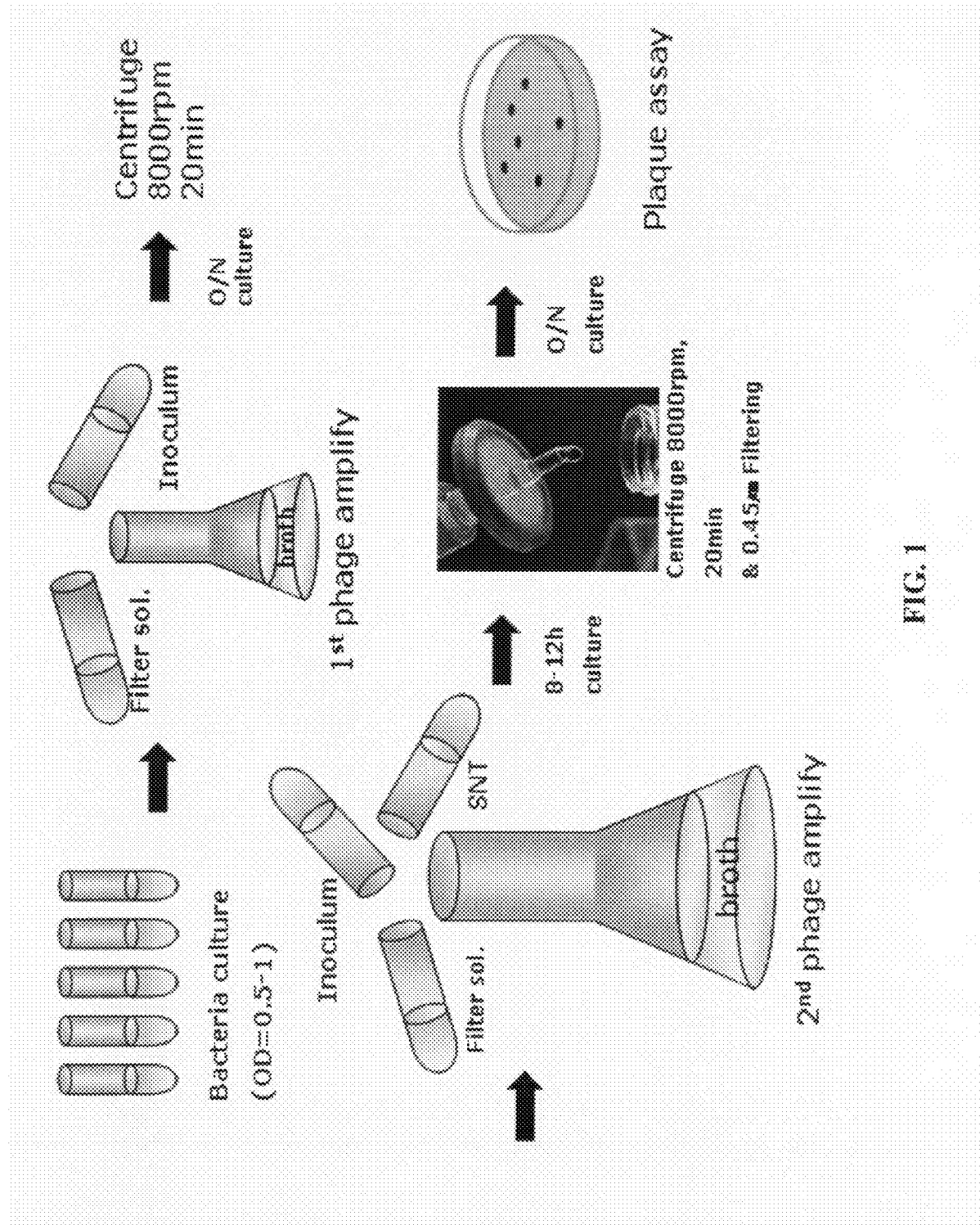
FIG. 1 is a schematic diagram illustrating the isolation method of the bacteriophage having killing activity specific to *Staphylococcus aureus*.
Figure 2:
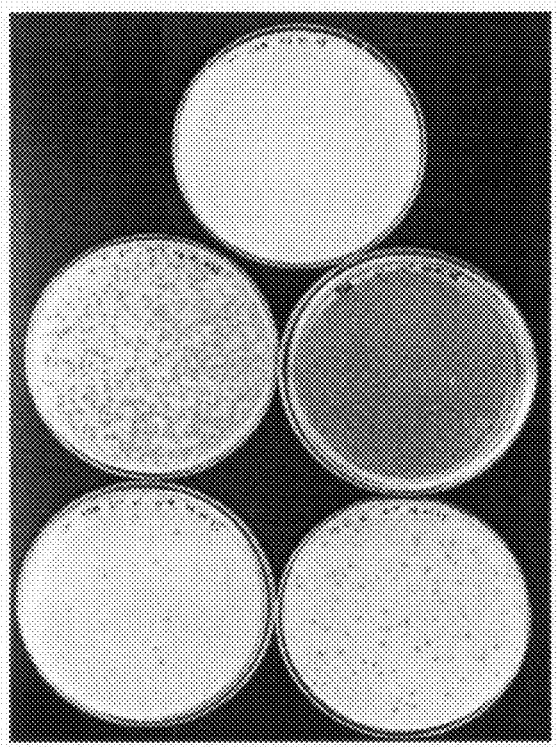
FIG. 2 is a photographe showing the result of plaque assay.
Figure 3:
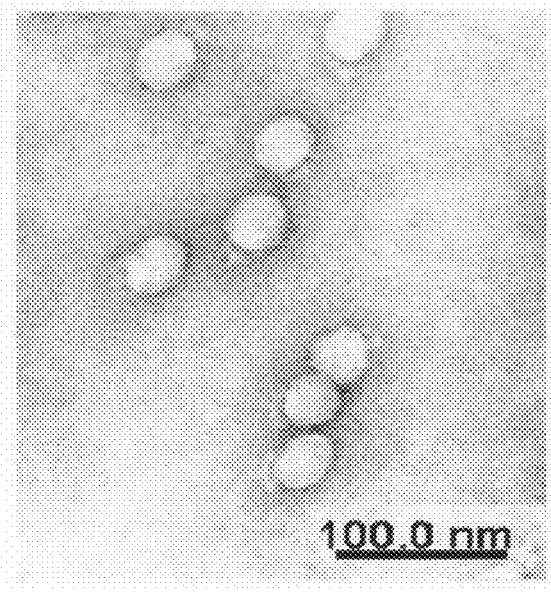
FIG. 3 is an electron microphotograph showing the *Staphylococcus aureus* specific bacteriophage detected by plaque assay.

Particularly, to isolate the bacteriophage having killing activity specific to *Staphylococcus aureus*, samples were collected from soil and straw in a cowshed and sewage where the bacteriophage was expected to be. The samples were shaking-cultured with *Staphylococcus aureus* at 37° C. for 3-4 hours. Centrifugation was performed for 20 minutes at 8,000 rpm to obtain supernatant. The supernatant was filtered with a 0.45 μm filter. The *Staphylococcus aureus* specific bacteriophage was detected from the filtrate by plaque assay. The method used for the assay is shown in the schematic diagram of FIG. 1 and the results are shown in FIG. 2. To observe the morphology of the obtained bacteriophage, CsCl density gradient (density: 1.15 g/ml, 1.45 g/ml, 1.50 g/ml and 1.70 g/ml) centrifugation (38,000 rpm, 22 hours, 4° C.) was performed, leading to the purification of the bacteriophage. The purified bacteriophage was loaded in a cupper grid, followed by negative staining with 2% uranyl acetate and drying. The morphology was observed and photographed under electron microscope. As a result, the isolated bacteriophage was confirmed to be the one belonging to φ29-like virus genus, Podoviridae family according to the morphological classification method (FIG. 3). The size of the bacteriophage was approximately 36.4 nm and named bacteriophage SAP-2.

Example 2

Genetic Characteristics of the *Staphylococcus aureus* Specific Bacteriophage

Figure 4:
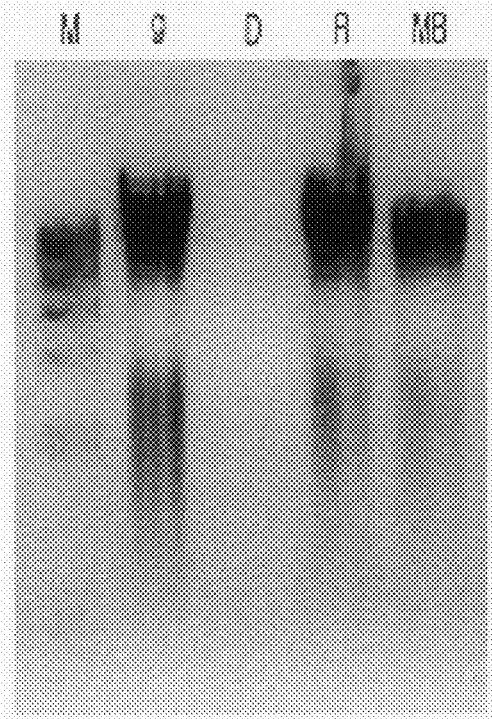
FIG. 4 is a diagram illustrating the characteristics of the genome extracted from bacteriophage; lane g: non-treated genome, lane D: genome treated with DNase I, lane R: genome treated with RNase A, lane MB: genome treated with mung bean nuclease, and lane M: molecular size marker.

Nucleotide sequence of the obtained bacteriophage SAP-2 was analyzed. First, the genome of the bacteriophage SAP-2 was extracted by the conventional method, and genetic characteristics thereof were investigated. Particularly, 50 ml of *Staphylococcus aureus* suspension ($OD_{600}=1$) and 1 ml of filtered bacteriophage suspension ($1 \times 10^8$ pfu/ml) were added into 200 ml of TSB (Tryptic Soy Broth) medium (casein digest, 17 g/l; soybean digest, 3 g/l; dextrose, 2.5 g/l; NaCl, 5 g/l; dipotassium phosphate, 2.5 g/l) in a 1 l flask, followed by shaking-culture at 37° C. for 3-4 hours. Then, lysis of *Staphylococcus aureus* was observed. After confirming lysis, the culture broth was filtered with a 0.45 μm filter. To eliminate DNA and RNA of *Staphylococcus aureus* remaining in the filtered culture broth, DNase and RNase (200 U each) were added to 10 ml of the filtered culture broth, which stood at 37° C. for 30 minutes. To inactivate the enzymes (DNase and RNase) therein, 500 μl of 0.5 M ethylenediaminetetraacetic acid (EDTA) was added thereto, which stood for 10 minutes. Next, to destroy outer wall of bacteriophage, 100 μl of proteinase K (20 mg/ml) and 500 μl of 10% sodium dodecyl sulfate (SDS) were added thereto, followed by incubation at 65° C. for 1 hour. After one hour incubation, 10 ml of phenol:chloroform:isoamylalcohol mixture (25:24:1) was added thereto and mixed well. The mixture was centrifuged at 18,000 rpm to separate layers. Upper layer was recovered, to which two times the volume of 100% cold alcohol was added, followed by extraction of pure genome. To investigate whether the genome extracted from bacteriophage was DNA or RNA, DNase I (10 U/μl) and RNase A (10 μg/μl) were added respectively, followed by incubation at 37° C. for 1 hour. The genome was also treated with mung bean nuclease (45 U/μl) for 15 minutes at room temperature to determine whether it was a single stranded DNA or a double-stranded DNA, in case it would be confirmed to be DNA. Electrophoresis was performed with those treated samples using 0.8% agarose gel and fragmentation pattern by each enzyme was investigated. As a result, the obtained genome was sensitive to DNase I (FIG. 4). The sensitivity to DNase I indicated that the genome was DNA and the non-sensitivity to mung bean nuclease indicated that the genome was a double stranded DNA. Therefore, it was confirmed that the genome of the bacteriophage was a double stranded DNA.

Figure 5:
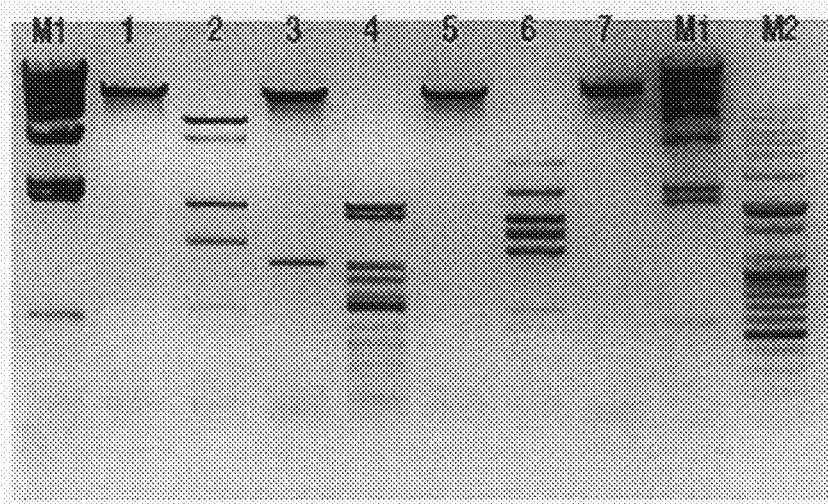
FIG. 5 is a diagram illustrating the fragmentation profiles of the genome extracted from bacteriophage by restriction enzymes; lane M1: molecular size marker, lane 1: fragmentation profile by Sal I, lane 2: fragmentation profile by Nde I, lane 3: fragmentation profile by Mbo I, lane 4: fragmentation profile by Dra I, lane 5: fragmentation profile by BamH I, lane 6: fragmentation profile by Acc I, lane 7: gDNA of bacteriophage SAP-2, and lane M2: molecular size marker.
Figure 6:
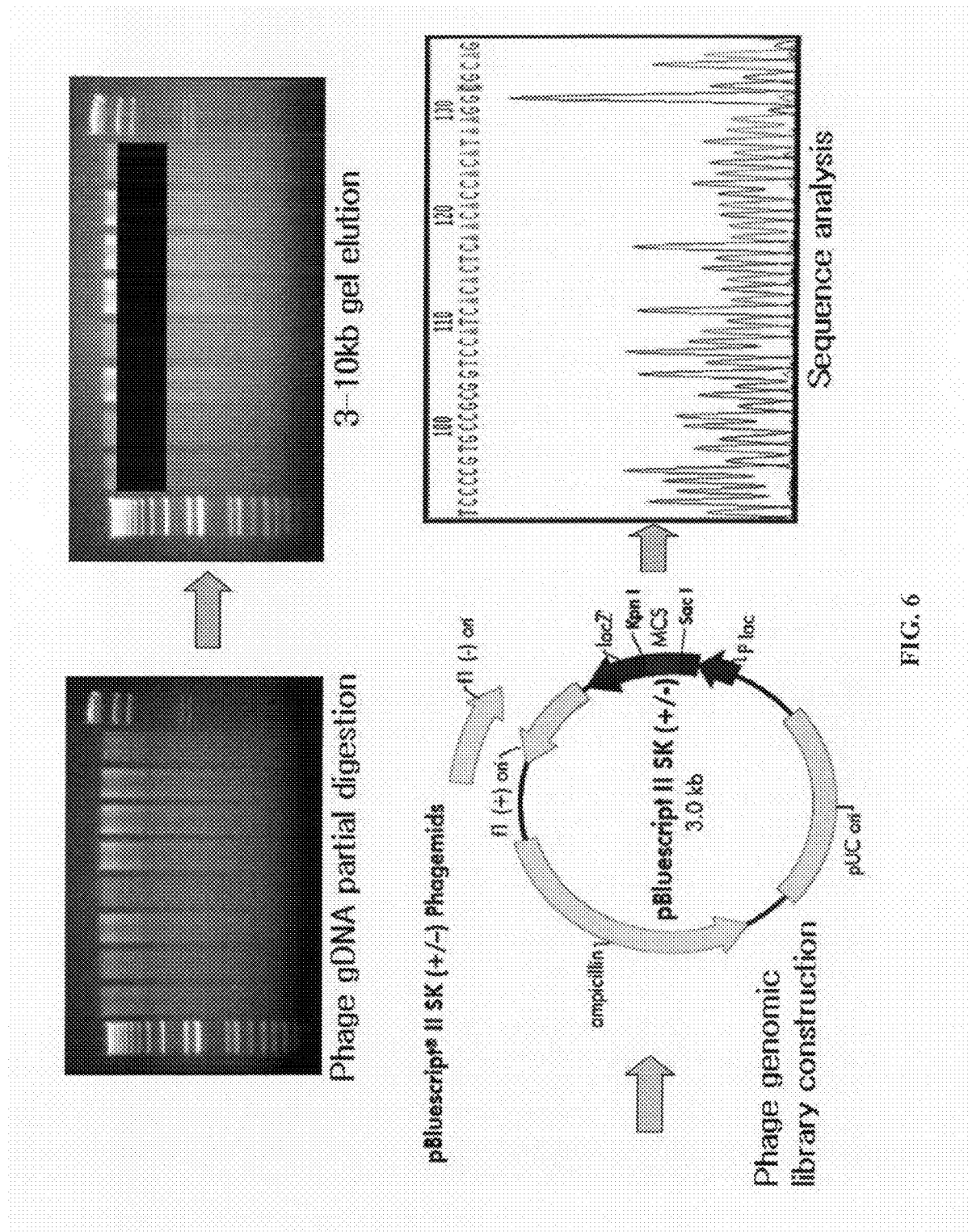
FIG. 6 is a schematic diagram illustrating the construction procedure of the bacteriophage genome library.

The genome extracted from the isolated bacteriophage was a genomic DNA (gDNA). To analyze the gene sequence of the gDNA, the genome was treated with several restriction enzymes and fragmentation patterns by these enzymes were observed (FIG. 5). Nde I was considered to be most appropriate for the construction of gDNA library. Thus, gDNA library was constructed by the conventional method using Nde I-treated DNA fragments. The method for the construction of gDNA library is shown in FIG. 6. Direct sequencing of gDNA of bacteriophage SAP-2 was performed to identify the whole nucleotide sequence of bacteriophage genome.

Particularly, DNA fragments were obtained by treating the gDNA of bacteriophage SAP-2 with Nde I according to the conventional method. Vector fragments were also prepared by treating the modified pGEM T-easy vector (Promega) with Nde I. The pGEM T-easy vector was the vector designed for TA-cloning. So, the vector could not be used as it was. Instead, T-overhang of the end of the vector was eliminated by the conventional method known to those in the art and then blunt-ended ligation was carried out, resulting in a circular modified vector. The DNA fragments and the vector fragments derived from the modified vector were ligated using T4 ligase. The resultant recombinant vector having the DNA fragment of bacteriophage SAP-2 was introduced into *E. coli* Top10F' via electroporation, a kind of electro-transformation. The transformant transformed with the vector was selected on the agar plate medium containing ampicillin supplemented with X-Gal (5-bromo-4-chloro-3-indolyl-beta-D-galactopyranoside) and isopropyl β-D-1-thiogalacto-pyranoside (IPTG) by using Blue-White colony selection. The selected single colony was inoculated into the medium containing ampicillin, followed by shaking-culture for overnight. Plasmids were extracted from the culture cells above using a plasmid purification kit (iNtRON). The extracted plasmids were electrophoresed using 0.8% agarose gel to confirm the size. Based on the size, recombinant plasmids were selected.

The numbers of selected plasmids were 3 in total and thus the numbers of clones obtained were also 3. The clones were cultured again and plasmids were extracted from the culture cells by the same manner as described above and the nucleotide sequences of the extracted plasmids were analyzed. Direct nucleotide sequencing of the gDNA of bacteriophage SAP-2 was also performed. Sequences of primers used herein are shown in Table 2.

TABLE 2

| Primer | Nucleotide sequence |
|---|---|
| T7 promoter | TAATACGACTCACTATAGGGCGA (SEQ ID NO: 2) |
| SP6 promoter | GTATTCTATAGTGTCACCTAAAT (SEQ ID NO: 3) |
| 1 | CGTAATGCTTCAAAATGTTC (SEQ ID NO: 4) |
| 2 | GAGCAATGTTAGTTGATTACTCATT (SEQ ID NO: 5) |
| 3 | CCATTTAAAAAATAATCATCACGTT (SEQ ID NO: 6) |
| 4 | TGCAATTCATATATTAGATGATAA (SEQ ID NO: 7) |
| 5 | TATGCTTTATATGGAGGTTGATAAC (SEQ ID NO: 8) |
| 6 | AATTAGTGTACCGTCACCTAAAGA (SEQ ID NO: 9) |
| 7 | TGCAACACCATCGTGATGTA (SEQ ID NO: 10) |
| 8 | GTTGTTGAACATCGCAACAG (SEQ ID NO: 11) |
| 9 | CAAAATCTGATAAAAACGTCAT (SEQ ID NO: 12) |
| 10 | GACGTGATGAGGATTATTAT (SEQ ID NO: 13) |

TABLE 2-continued

| Primer | Nucleotide sequence |
|---|---|
| 11 | ATAAATTCTCTTTCTTTTTCCTCAAATTCAAATCTCG CTAATGT (SEQ ID NO: 14) |
| 12 | CATACGTGGATAATTACGTTTCAACATTAATTCCTCA TTT (SEQ ID NO: 15) |
| 13 | ATCAAATTCATTTAAAATTTTCTTTCT (SEQ ID NO: 16) |
| 14 | AATGTCACCTATGTTTAATGCAGA (SEQ ID NO: 17) |
| 15 | AGTTCATCATTTAAGAATTGAACAACAGAACT (SEQ ID NO: 18) |
| 16 | TTTGTTGCTCTAATGATGTAATACGTTGTTCTAATAT AACAG (SEQ ID NO: 19) |
| 17 | TCACTTGCAATAATACCACTTTCTAAT (SEQ ID NO: 20) |
| 18 | GTCAAGTATCATTTTAATACAATTT (SEQ ID NO: 21) |
| 19 | TCATTATACATTACGTGACGCTTA (SEQ ID NO: 22) |
| 20 | AGCTTCTCTTTCTTTTTTCCATCTA (SEQ ID NO: 23) |
| 21 | GAACTTCATTGTATTTAGCGCTGTTG (SEQ ID NO: 24) |
| 22 | TGAATCTTCATATGGTCGACCTGCAG (SEQ ID NO: 25) |
| 23 | ATTTAATAGTTTTGCACAAGTACCAA (SEQ ID NO: 26) |
| 24 | CAAACTAACCCATCTGATAAACAAAC (SEQ ID NO: 27) |
| 25 | AACCTAATGGCTATTGGTTCCAACCA (SEQ ID NO: 28) |
| 26 | GGTAACAGTTCAGTTAATTCACAT (SEQ ID NO: 29) |
| 27 | GGTGCCATAATTTATTATTCCTCC (SEQ ID NO: 30) |
| 28 | TTAATCGTACCTAATTTAATATCAC (SEQ ID NO: 31) |
| 29 | AACGTAAATCGTTATTACTTGCAATG (SEQ ID NO: 32) |
| 30 | CGTTACAACACCCGGAGAATATTA (SEQ ID NO: 33) |
| 31 | CCAAATGTCCAAGATTTTGAATAA (SEQ ID NO: 34) |
| 32 | TTTAAAATGTACAGGTACGTATAC (SEQ ID NO: 35) |
| 33 | TTGAATTTAACGAATATAATTTGGC (SEQ ID NO: 36) |
| 34 | ATATTATCATGATTGCACATAACTG (SEQ ID NO: 37) |
| 35 | GTAAAAGGTTATGGACGTTTTAAT (SEQ ID NO: 38) |
| 36 | AATTTTTATGACTATATAAAATCATT (SEQ ID NO: 39) |
| 37 | ACAAAAAACATTTAACAACACGTAT (SEQ ID NO: 40) |
| 38 | AAATAAAATACAAAACATAATCAAT (SEQ ID NO: 41) |

The nucleotide sequence of the total genome of the bacteriophage SAP-2 obtained by the above two methods was represented by SEQ. ID. NO: 1. The total number of nucleotides forming the genome of bacteriophage SAP-2 was 17938.

Example 3

An Example of the Application of the Staphylococcus aureus Specific Bacteriophage SAP-2 for the Prevention of Staphylococcus aureus Infection 100 µl of bacteriophage SAP-2 suspension ($1 \times 10^8$ pfu/ml) prepared in Example 1 was added into 9 ml of nutrient broth (beef extract 3 g/l, peptone 5 g/l). A control medium was prepared without the addition of the bacteriophage suspension.

Staphylococcus aureus suspension was added into each medium at a starting optical density at 600 nm ($OD_{600}$) of 0.5, followed by investigation of the growth of Staphylococcus aureus. As shown in table 3, in the medium not treated with the bacteriophage suspension, Staphylococcus aureus was growing so well (30 minutes later: $OD_{600}$=0.8). On the other hand, in the medium treated with the bacteriophage suspension, Staphylococcus aureus was not grown at all (10 minutes later: $OD_{600}$=0.1, 60 minutes later: $OD_{600}$=0.05). It was confirmed from the above results that the bacteriophage SAP-2 isolated in Example 1 was very effective in the prevention of the infection of Staphylococcus aureus.

TABLE 3

| | Staphylococcus aureus killing activity ($OD_{600}$) | | |
|---|---|---|---|
| | Starting optical density | 10 minutes of culture | 60 minutes of culture |
| Control (non-treated) | 0.5 | 0.6 | 0.8 |
| Experimental group (treated with the bacteriophage suspension obtained in Example 1) | 0.5 | 0.1 | 0.05 |

Example 4

An Example of the Application of the Staphylococcus aureus Specific Bacteriophage SAP-2 for the Treatment of an Infectious Disease Caused by Staphylococcus aureus 10 dairy cows infected with mastitis caused by Staphylococcus aureus were selected to investigate the effect of bacteriophage SAP-2 isolated in Example 1 on treatment of mastitis. The cows were divided into two groups (5 cows per group). 10 ml of bacteriophage SAP-2 suspension ($10^8$ pfu/ml) was sprayed on the lesion of dairy cows in one group every day and 10 ml of PBS without the bacteriophage was sprayed on the other group every day with same manner, particularly on the infected regions. The spray was continued for 10 days. As a result, significant treatment effect was observed in the group sprayed with the bacteriophage suspension. From the result, it was confirmed that bacteriophage SAP-2 isolated in Example 1 was very effective in the treatment of the infectious disease caused by Staphylococcus aureus.

TABLE 4

Treatment effect on disease caused by *Staphylococcus aureus* infection (number of *Staphylococcus aureus*)

|  | Before treatment | After treatment |
|---|---|---|
| Control (PBS) | $1.5 \times 10^4$ cfu/ml | $1.7 \times 10^4$ cfu/ml |
| Experimental group (treated with the bacteriophage suspension obtained in Example 1) | $1.7 \times 10^4$ cfu/ml | $1.2 \times 10^2$ cfu/ml |

Example 5

Comparison of Bacteriolytic Activities of *Staphylococcus aureus* Specific Bacteriophages The present inventors compared bacteriolytic activities between the two *Staphylococcus aureus* specific bacteriophages (KACC 97001P and KCTC 11154BP). The target *Staphylococcus aureus* strains were provided from Culture Collection of Antimicrobial Resistant Microbes, Seoul Women's University, Seoul 139-774, Korea. And the results are as shown below.

TABLE 5

| No. | CCARM No. | Species | A | B |
|---|---|---|---|---|
| 1 | 0027 | *Staphylococcus aureus* | ⊙ | ⊙ |
| 2 | 3501 | *Staphylococcus aureus* | ⊙ | ⊙ |
| 3 | 3502 | *Staphylococcus aureus* | x | ⊙ |
| 4 | 3089 | *Staphylococcus aureus* | ⊙ | x |
| 5 | 3090 | *Staphylococcus aureus* | ⊙ | ⊙ |
| 6 | 3091 | *Staphylococcus aureus* | ⊙ | x |
| 7 | 3095 | *Staphylococcus aureus* | ⊙ | x |
| 8 | 3108 | *Staphylococcus aureus* | ⊙ | x |
| 9 | 3207 | *Staphylococcus aureus* | ⊙ | x |
| 10 | 3209 | *Staphylococcus aureus* | ⊙ | x |
| 11 | 3210 | *Staphylococcus aureus* | ⊙ | x |
| 12 | 3222 | *Staphylococcus aureus* | ⊙ | x |
| 13 | 3223 | *Staphylococcus aureus* | ⊙ | x |
| 14 | 3224 | *Staphylococcus aureus* | ⊙ | x |
| 15 | 3229 | *Staphylococcus aureus* | x | x |
| 16 | 3230 | *Staphylococcus aureus* | x | ⊙ |
| 17 | 3267 | *Staphylococcus aureus* | x | x |
| 18 | 3268 | *Staphylococcus aureus* | x | x |
| 19 | 3270 | *Staphylococcus aureus* | ⊙ | x |
| 20 | 3271 | *Staphylococcus aureus* | ⊙ | ⊙ |
| 21 | 3467 | *Staphylococcus aureus* | x | x |
| 22 | 3468 | *Staphylococcus aureus* | ⊙ | ⊙ |
| 23 | 3469 | *Staphylococcus aureus* | x | x |
| 24 | 3476 | *Staphylococcus aureus* | x | x |
| 25 | 3504 | *Staphylococcus aureus* | ⊙ | x |
| 26 | 3521 | *Staphylococcus aureus* | x | x |
| 27 | 3531 | *Staphylococcus aureus* | x | x |
| 28 | 3533 | *Staphylococcus aureus* | x | x |
| 29 | 3535 | *Staphylococcus aureus* | ⊙ | ⊙ |
| 30 | 3538 | *Staphylococcus aureus* | x | x |
| 31 | 3543 | *Staphylococcus aureus* | x | x |
| 32 | 3547 | *Staphylococcus aureus* | ⊙ | x |
| 33 | 3548 | *Staphylococcus aureus* | x | x |
| 34 | 3549 | *Staphylococcus aureus* | ⊙ | ⊙ |
| 35 | 3554 | *Staphylococcus aureus* | ⊙ | x |
| 36 | 3557 | *Staphylococcus aureus* | x | ⊙ |
| 37 | 3596 | *Staphylococcus aureus* | ⊙ | x |
| 38 | 3599 | *Staphylococcus aureus* | x | □ |

In the Table, CCARM No. indicates reference number used at Culture Collection of Antimicrobial Resistant Microbes, "□" indicates bacteriolytic activity confirmed and "x" indicates no bacteriolytic activity. "A" illustrates the result of the bacteriophage deposited under accession number of KACC 97001P and "B" illustrates the result of the bacteriophage deposited under the accession number of KCTC 11154BP.

As shown in the above results, two different bacteriophages exhibited bacteriolytic activity against different kinds of *Staphylococcus aureus*. In the case when they showed equal bacteriolytic activity, the activity level was quite different. So, two different bacteriophages above were complementary each other and thus the cocktail of the two was believed to increase antimicrobial effect. In most cases, bacteriophages had different bacteriolytic mechanisms.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An isolated Podoviridae family φ29-like virus bacteriophage deposited under the Accession No. KCTC 11154BP, which has killing activity specific to *Staphylococcus aureus*.

2. The bacteriophage according to claim 1, wherein the bacteriophage has the genome represented by SEQ. ID. NO: 1.

3. A pharmaceutical composition for the prevention and treatment of a disease caused by *Staphylococcus aureus*, containing the bacteriophage of claim 1 as an active ingredient.

4. A pharmaceutical composition for the prevention and treatment of a disease caused by *Staphylococcus aureus*, containing the bacteriophage of claim 2 as an active ingredient.

5. The pharmaceutical composition according to claim 3, wherein the disease caused by *Staphylococcus aureus* is selected from the group consisting of mastitis, acute dermatitis, sepsis, pyogenic disease, food poisoning, pneumonia, osteomyelitis, impetigo, bacteremia, endocarditis and enteritis.

6. The pharmaceutical composition according to claim 4, wherein the disease caused by *Staphylococcus aureus* is selected from the group consisting of mastitis, acute dermatitis, sepsis, pyogenic disease, food poisoning, pneumonia, osteomyelitis, impetigo, bacteremia, endocarditis and enteritis.

7. An antibiotic containing the bacteriophage of claim 1 as an active ingredient.

8. An antibiotic containing the bacteriophage of claim 2 as an active ingredient.

9. A disinfectant containing the bacteriophage of claim 1 as an active ingredient.

10. A disinfectant containing the bacteriophage of claim 2 as an active ingredient.

* * * * *

SEQUENCE LISTING

<160> NUMBER OF SEQ ID NOS: 41

<210> SEQ ID NO 1
<211> LENGTH: 17938
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 1

```
taaatataat cggaaaaagt ttttgtaaat ttacacctcc ccaccgttta aaataaacga      60
ttatacaaat caaaacttat aaattaactt atcatttcta aactaaactt ataaaaaatg     120
ttcacctact ttcccaactt atctaaccta ttacatattc attaattaca aaatatatac     180
atctattgac ttttatccaa aattatgatt tgaaattaaa atctagtttc ttctattaaa     240
tagtagtttt aaattattta aacttttta cgatatttta ttgacaaaac atttaaacat      300
```

```
ttgctatact aagtatgtaa tcaaaacaag gaggtaacaa aaatgattaa tgttgataat    360
gcaccatcag aaaaaggtca agcatatact gaaatgttgc aattattcaa taaactgatt    420
caatggaatc cagcatatac gtttgataac gcaattaact tagtatctgc ttgtcaacaa    480
ctattattaa actataacag ttctgttgtt caattcttaa atgatgaact caacaacgaa    540
actaagccag aatctatttt agcttatatt gctggtgacg atgcaatcga acagtggaat    600
atgcacaaag ttttttatga aacgtataat gtttacgtat tttagaaagg aatgatataa    660
tgaaagctga tgacattata actttacgtg ttaaaggtta tatattccat tacttagatg    720
aatcaaatga atacattgaa gaatttatac cacttcacga gtatcattta actaaaacac    780
aagcaataga attattacct aacacatgta cactattatc aactacacgc aaaacgaaaa    840
aaatccaagt atattacaat gatttactac aaatttcaat taaagaggag aaataaaaaa    900
tgacaaacgt aaaagaaatt ttatcaagac accaaaatac aacagcgaga tttgaatttg    960
aggaaaaaga aagagaattt ataaaactat cagaattagt tgaaaaatac ggtattaaaa   1020
aagagtatat cgttagagca ttattcacaa acaaagaatc aaaattcggt gtacagggtg   1080
ttatcgtcac tgacgactat aatgtaaact taccgaacca cttaacagag ttaattaaag   1140
aaatgagatc agacgaggac gttgttaaca ttatcaatgc tggtgaagtg caatttacaa   1200
tttatgaata tgaaaacaaa aaaggtcaaa aaggttactc aatcaacttt ggtcaagtat   1260
cattttaata caatttcata ggggatattt atcccctatt ttatgaggtg ctaaacaatg   1320
gaaaaaatat acactgccgt attattatac aatgtatcaa ttaatgaaac atatgaacat   1380
gaaattgaac aattcgaaaa aataaataaa gttaaggtaa tatatagtta ttttgacgca   1440
aactttacaa aaaaggtgc atataatttt ggtgtaaaat acattaagga gatataaaaa   1500
tgaatattac aacaacatta aacacaaaaa aattaattaa ttatatttta gataatagag   1560
attgttttat gaataaaata acaaaattta catcactaag tggaaaatgt gttgttttg    1620
ttagatacgg tgaaatttct attgaatact atgatagtga tacaaaaaac aataatgatt   1680
tatttacttt agacattgac gttgatatta ataaacatgt ctttaattgt cttaaagttt   1740
attatataga acatacagaa gatataaaca taatatataa aaaaggtgta tacatggggt   1800
gtactattga tgatgtatta tcatattttg aaaaaccatt agaaagtgat attactatta   1860
tttaccaagg caaagttatt tatgaatacg ggaaagtaat agaccatgaa taacctacta   1920
gatattatta ttgttttcct tttagcattt ttaattacac ttgtaatact tatgacaatg   1980
tatatacgtg tgtcatttgg tgtttttatt actacattta ttatattcta cattatcttt   2040
ttattggttg tatatgcttt atatggaggt tgataacatt ggtttagaca tacgtctgaa   2100
atggatagat ggaaaaaaga aagagaagct agaaagaaa gagaagaaaa aaatataaaa   2160
aatgatttta gcggtatcaa ttttaaattt gacgataaag atttacaaga ggcttatatt   2220
gacgcatgga aacatttttc acatttacca catttaccaa agaaaaaaaa tgtatctcat   2280
gcaaacgctg tttcattagt tcgtggtaaa cgacataaaa aattaaatca tatactagaa   2340
atatataacc gtaatgataa taataacaaa aatgcaaaaa tgcataaata tgcattatat   2400
aatttacacg ccgaaaaaaa taaatcttca cttacaaaat atattaaaga aattgataac   2460
ttatttttg aaataggaaa atcagataga ccaaaaacaa caatagatga tatcaatgtt   2520
aggtataact ttttatatta tgcaacattt gaagaataac tttaatactg taaatgacat   2580
tataaactat tacaaggagc aaaaacatgg tgaaacaaaa tcgtttagac atggtaagag   2640
attatcaaaa tgcggtcaat catgtaagga aaaaaatacc agaaaactat aatcaaatag   2700
```

```
aattagttga tgaactcatg aatgatgata tagactatta tatatctatt tcaaaccgtt    2760
ctgacggaaa atcgttcaac tatgtttcat tttttattta tttagctatt aaacttgata    2820
taaaatttac tttattatca cgtcattata cattacgtga cgcttaccgt gattttattg    2880
aggaaatcat agataaaaac ccactattca aatctaagcg tgtcactttc agaagcgcta    2940
gagattattt agctattatc tatcaagata aagaaattgg cgtgattaca gatttgaata    3000
gcgctactga tttaaaatat cattctaact ttttaaaaca ctaccctatt attatatatg    3060
atgaattctt agcgcttgaa gatgactatt taattgatga gtgggacaag ttaaaaacaa    3120
tttatgaatc aatcgaccgt aaccatggta atgttgatta tattggtttt cctaaaatgt    3180
ttttactagg taatgctgtc aacttttcaa gtcctatatt atccaattta aatatttata    3240
atttattaca aaaacataaa atgaatacat caagacttta caaaaacatt tttttagaaa    3300
tgcgtcgaaa cgattacgtc aatgagaggc gtaatacacg tgcgtttaat tcaaatgatg    3360
acgctatgac aactggcgag tttgaattta acgaatataa tttggcagat gataatttaa    3420
gaaatcatat caaccaaaac ggtgattttt tctatattaa aactgacgat aaatatataa    3480
aaattatgta taatgttgat acatttaatg ctaacatcat tgtaataccct tatacaaaac    3540 aatatgagtt ttgcactaaa atcaaagata tcgatgacaa tgttatttat ctaagagaag    3600
atatgtttta taagaaaaac atggaacgat attactacaa tccaagtaat ttacattttg    3660
acaatgctta ttcaaaaaat tacgtggttg ataatgatag atatttatat ttagatatga    3720
ataaaattat aaaatttcat ataaaaaatg aaatgaagaa aaatattaac gaatttgaaa    3780
gaaaagaaaa gatatacgaa gataactata tagaaaatac aaagaagtat ttaatgaaac    3840
aatacggctt ataaaaggtg tgtaagatta tgggattact tgagtgtatg caatatcata    3900
aaaatcaacg taaaatgata ttgtactggg atattgaaac attatcgtac aataaaataa    3960
acggacgcaa taaccaaca ttatataaaa acgtaacgta ttctgttgcg attggttggt    4020
ataatggtta cgaaattgat gttgaagtat tccccagttt tgaagccttt tatgatgatt    4080
ttttcaagta tgtttatcgc cgggatacaa tcacaaaatc aaaaacaaat attatcatga    4140
ttgcacataa ctgtaataaa tacgataatc atttttttact taaagacacc atgcgttatt    4200
ttgataatat tacacgcgaa aatgtatatt taaaatctgc agaagaaaat gaacatacaa    4260
taaaaattca agaggctact attttagcca aaaatcaaaa tgtgatttta gaaaaacgtg    4320
ttaaatcttc aatcaattta gatttaacga tgttttttaaa tggttttaaa tttaatatca    4380
ttgataactt tatgaaaacc aatacatcaa tagcaacatt aggaaaaaag ctacttgacg    4440
ggggttattt aacagaaaac caacttaaaa cagatttttaa ttatacaatt tttgataaag    4500
ataacgatat gtcagatagt gaagcttatg actatgctgt taagtgtttt gataatctta    4560
catctgaaca attaacctac attcataatg acgtgattat attaggtatg tgccatattc    4620
attatagtga catttttcca aattttgact ataacaaatt aacattctca ctaaatatca    4680
tggaatctta tttgaataat gaaatgactc gttttcagtt actcaatcaa tatcaagata    4740
ttaaaatatc ttatacacat tatcattttc atgatatgaa ttttttatgac tatataaaat    4800 cattttatcg tggtggttta aatatgtata ataccaaata tatcaataaa cttattgatg    4860
aaccttgttt ttctatagac atcaattcga gttatcctta cgtgatgtat catgagaaaa    4920
ttccaacatg gttatacttt tatgagcatt actcaaaacc aacattaatc cctacttttt    4980
tagatgatga taattatttt tcattatata agattgataa agaggtattt aacgatgagg    5040
tattaattaa aatcaaatca cgcgtactac gtcagatgat tgttaaatac tacaataatg    5100
```

```
ataacgatta cgttaatatc aatacaaaca cattaagaat gatacaagac attacgggta    5160
ttgattgcac gcatatacgt gttaattcgt ttgttgtata tgaatgtgaa tactttcacg    5220
cacgagatat tatatttcaa aactatttta ttaaaacaca aggtaaatta aagaataaaa    5280
tcaatatgac aacaccttac gactatcaca ttacagatga aattaacgaa caccccttact   5340 caaatgaaga agttatgtta tcaaaagtcg ttttaaatgg tttatatggt atacctgctt    5400
tacgttcaca ctttaattta tttcgtttag atgaaaacaa cgaattgtat aacatcatta    5460
acggatacaa aaacacggaa cgtaatattt tattctctac atttgtcaca tcacgttcat    5520
tgtataactt attagtacct ttccaatact aacggaaag tgaaattgac gacaatttta     5580
tttattgcga cactgatagt ttgtatatga aatcagttgt aaagccctta ttgaacccca    5640
gtttattcga ccctatatca ttaggcaaat gggatattga aaacgaacag atagataaga    5700
tgtttgtact gaatcataaa aaatatgctt atgaagtgaa tggaaagatt aaaattgcgt    5760
ctgctggtat accgaaaaac gccaaaaata caagcgtcga ttttgaaacc tttgtacgtg    5820 aacaatttt tgacggtgca attatagaaa acaataaaag tatctataat aatcaaggta     5880
cgatatcaat ttatccgtca aaaacagaaa ttgtttgtgg taatgtatat gatgaatatt    5940
ttactgatga acttaattta aaacgtgaat ttatcttaaa agacgctaga gaaaattttg    6000
accatagtca atttgatgat attctttata ttgaaagtga tattggttca ttttcactca    6060
atgacttatt tccatttgaa cgttcagtac ataacaaatc tgatttgcat atattaaaac    6120
aacaacatga tgacatcaaa aaaggcaact gttaaaataa cagtcgcctt ttctttgaga    6180
taacatgaaa aatgtgtacg aaaattgatt atgttttgta ttttatttac tagcattact    6240
agcatgtgtt cattatagca taaatcttta tgcaatacca ctaaagaata caatattatc    6300
acctgcgttt tctggtacac cgttaatgag tgtatacaat aatacgtg acggtgcaac      6360 gtatggtggt acattatagt ttgcgactaa gaatgaacca tcgtcaaaca cagcaacaac    6420
tacacccgtg tgaccgatac catatatgct tgcttgtaag tatggcggtt tactagagaa    6480
gccgtaacca acggtaggaa tatgtgttgt tttagccct aattttttat aaacatacca     6540
cacacgttga ccgtttgtta cttgtccatc atcagttggt tgtcttttc catgtaattg     6600 tgacatatac gcccatgtta attctgtaca ctgaccagca ttaccagttt gagggaatat    6660
gttacccggt ttgtataaat attctttttt gaataaaggt acaccaattg cttttttata    6720 ttttctggt aattggtcat acgtccagtt accacctatc acacgaccac ttttccgtt     6780 tggtttcaca gatttacctc taatcgcatt atgctcacca tcgtcatcag tagggttga    6840 acttccaccg tcatctattt gcacactatc aatgagcttt tttaatgagt cgagtagtcc    6900
aatcgtcatt ttaatatgat acgtgttgtt aaatgttttt tgtagtgtaa ataatcatt    6960 actaaaaaat ttatcactac caatactatg cacgtcccat tgtaatgcgt cttgaacttt    7020 tttaataat tcttgcatgg cttgttttgc taaagcgagc agtgaactac cactgtcacc     7080
actactacca ctgtcagacg aatcactagg tgaaccacct ttaccgtcta atttaccacc    7140
ccatgctaaa atagtatttg caccgtctaa aaaaggatta ccatagtttt gtactttatt    7200
atatgacgct ttcaaaccta ggggataata tgccgcccaa gtagctgcag ccgttaatgg    7260
gatataagca cgtccaaccg taccagcttt catgttttta gcaaaatctg cattacctt    7320 tctttgtacg ttttgaggta caaagtgaac gatgttacct gcgtcatacc aagacggttg    7380
tcctgcttgt tttgattgtg atacaagctt tctagctaca aatttagcgt ctgttaaata    7440
atcgccttgt gcagaagtat gatttaacca acctaaacct gcactgtatc cttcgttttt    7500
```

```
ttcatataca gcaattagcg taggtgaaac tcctatcgat ttaactgcat ttagaacttg    7560
tctgatttta ctttcattac cacctaacca aacattaaaa cgtccataac cttttacttt    7620
aggcactaac tggtctatcg ttaatccaaa gtcatcatta ataagaat gtgtaaattt      7680 atctatcttc tcttggtcgt tcatctttat cactcttttc agaatcgttt ttaattactc    7740
ttaatttatc tttaatttgt tctggcacta atacatccat ctctgcacaa ttttctacaa    7800
tagataaacc ctcattagca atataataga aaatcgtaat cataagtaga ccaccttta     7860 attgtaaaat ttggtcaatg atatttgcta gaataataat acagaatatg agtaattttt    7920
tagcgaaacc tctcattgat ttttttgacc atagattatt atttttaatg gcttttgaaa    7980
tacctgtaat aatatcaaca aacattaata taaataaaaa atatagtaat tttaaatctc    8040
ctgcatatat aaacatgtga aacacttctg tatctgtaaa cctgaatttt acttcattca    8100
tttttatacc ccctctctaa atttattatt taatggattt tgtaacatag ggttacctga    8160
accatcatta tgccaaaatc tcacaccaga ttccaaaata gcttttaatt gttccattaa    8220
catagggtca atgtcacgta ttgtatacgt acctgtacat tttaaatagt tgcatatagt    8280
catactgtta attggttcaa taaatgtatt atagtcattt acttcaaaac caaacaacat    8340
ataatatttt tgtaaaaatg taatttcttt aggtgacggt acactaattt tcattgttaa    8400
accgttaatg ctatttgcga tttggaaagc gttccccatt tctgactctg tcactgatgg    8460
tggttgtaag gctaaatctt tatattctgc ttgttgttgt ttgtagaaat tatattcttc    8520
attaaactta ccaaataaag cagttggact taaattactt gctacactta cagcgtcata    8580
aaaacgtgat tttgggtcac tgccatttaa tacattatct atacgacttg tgattaattg    8640
actttctgca ttacgctgtc tattggcttg ttgtgattgc cctaaaatac cgttattgat    8700
taaaattggt acttgtgcaa aactattaaa tgttatattt gtatttaaga atgaacctgt    8760
atcaattaat atatctttat tttttgcaag tatcggtcta tcattttcag cactgttata    8820
atctactgga taaactcgca cttcattatg ataaccaatg atggattttg tacgtaactt    8880
aacacctgtt ttttgtgaaa tcttaccagc gtctagtaac atagtattac cattccagtc    8940
ataaaaatca atcgtcatgt actcattacg tatcatatgg tcgcactcgt cttttttaga    9000
caacatcatc tcttgaagct ttgtgaaact taatgataaa tcgtttaaac tccattcttt    9060 tgatttttcca cctgttttta acgtctttaa tccagtaatt ttttcacttg tcttaacgtc    9120
ctctaaatct tttgtattaa tagaatcttt aggtaacatt tgaaccttt gaaagttttg     9180 tgtaatccat ggataggcac tcattttatc cataaagtta ataagtcac catattccat    9240 aacgtataag ttgactggtg atgtgatatt gtcatatatt gtacctttag acgtatctaa    9300
gtttggctct ttttagtac caatttctt tgataaatca gcacttgact ggaataacac     9360 taaatttcc aaaactgtt gcatttggtt atacacatag ttttatttg atactttaa        9420 cacatcatca ttgttacgta acattggtaa catatagtta tacgtgcgtt ttgataagtg    9480
ttgacgttca atattaacgt ttgagagttg ttctaataca ttaccttgtg tatacgtcat    9540
aatagtatca atcacaaaat atattttaac cacaacatca ttcacatatt cgatttgatt    9600
cacaaacgca taataacgtc tgtcctcaaa atctgataaa aacgtcatgt agttaatccc    9660
ttgtgcgtca tgccactgca tatcaacatt gatttccatt ctatcacgta taaaattata    9720
cggttgtttg gaatagtcta atgatttaaa atgacgtcca tttaaaaaat aatcatcacg    9780
ttcttgatta ctattaaaat gaatcgtatt ttgataatca gtaaacggtg tgttatagaa    9840
aaatttaaaa tttgttaatt ttctcatttt tacctccata aaaaatagtc gtataaatta    9900
```

```
tttatacgac tattataaca tttttattca atgatttgtg tatctattgc aaaacttttta   9960
ttaccatttg aaagctcact atcactataa tttgatgtaa caaaatgtaa ttcattatta  10020
aagtttaaat ataatcttgt attaatcatt ttcgaatcaa tcgcacattg tgtgtagtga  10080
tgtgtagatt ttaagtttgc gttaatcgta cctaatttaa tatcaccgtt tttcttaatg  10140
cctttttaata cccctttttaa ttgtatggtt ttaacaccat taattgttaa aatacgatat  10200
tgcggtgcag gatatccaac gttgctatca cttgcaataa taccactttc taatgtaata  10260
tcttgccacc ctgtatcatt cacagttgtt ttatttttcat taattgtatt taaaatttct  10320
attttatcat tagttattat agcagttaaa ttgttaatac tttgtgtatt attacctaca  10380
ctttcttttg tagctataat atcttgttta ttttttttcaa tatcttcttc attttttgtg  10440
tttttatcat ctaatatatg aattgcagat tcatgattac ttagtttatt tgtatgttct  10500
gattgaacat ctgataaatt ttttatttttt ttatcttgtt gcacattatc ttctttaata  10560
ttaataatgt ctgtagcgtt ttgagaaata ttattttttat ttgtagcgat atcattttta  10620
tttttattaa tgtcttttgt gttcgtatta attttactta ataattcatc tttaaaggtt  10680
aacttataat aatcctcatc acgtcttata taaatgttac cgtcctttgt agtaattaag  10740
tcatttgctt ctactaaatt atcatttaat ttatctacag agtcaatgtt gcgcaaactt  10800
ccttaaaatc caacaaccat tggttaaacc ttttatttta atgttttcca actaattcaa  10860
agaaaaattc tattttatca ttagttttta tagcagttaa attgttaata ctttgtgtat  10920
tattacctac actttctttt gtagctataa tatcttgttt attttttttca atatcttctt  10980
cattttttgt gttttatcat ctaatatat gaattgcaga ttcatgatta cttagtttat  11040
ttgtatgttc tgattgaaca tctgataaat tttttatttt tttatcttgt tgcacattat  11100
cttctttaat attaataatg tctgtagcgt tttgagaaat attattttta tttgtagcga  11160
tatcatttttt atttttattt atgtcttttg tgttcgtatt aatttttactt aataattcat  11220
ctttaaaggt taacttataa taatcctcat cacgtcttat ataaatgtta ccgtcctttg  11280
tagtaattaa gtcatttgct tctactaaat tatcatttaa tttatctaca gagtcaatgt  11340
tgcgcaaact tcttacaatt ctatcagcca ttgtttacac ctcttattta tatcgtttcc  11400
aactaaattc aaagaaaaat cctaaaatac ccattatgag aacaccccccc aaggtacacc  11460
aatactatat gcattacctg tttttccgtt ccattgtcta actggtaaat aataacgagt  11520
tccttgccag ttataaccaa tccaaactaa cccatctgat aaacaaactt cgtcatatgg  11580
tgtatagccg tttggttgga accaatagcc attaggttca cttaatttag gactacagac  11640
acgtgcaaat attggtaaaa aaccacatgt aaatgttgcc ttttcgtttc tataatatgt  11700
gccgtattgg ttttgtttcc aattattagt tagttgaata ttttgttcta atactttact  11760
ttcactgttt gagaattttg ggcgaataaa atgtgtcaca ccgtcataat aatgtgttct  11820
aattgttgct ttttcccaac catcatatcc accattcaac cagttttgtt ctaaacatgt  11880
ataataatca agatttccac ttgttacaca ttggatatgt ccatattgag aatttgtgta  11940
tactgcaaca tcacctaatt gaggtttaaa gctcgatgta ttttcataca ccgttgctaa  12000
acctttaaag tcattattaa ttgcgtcttt agcattaccc cacatacgca ctttaccgtc  12060
agtaatataa tagatataag caacagctaa gtccatacat tgaaaaccat atgcaccatc  12120
aaagtcaaca ccaacacctt catgtttata tatccaatct ttagcttgtt gttgtgattt  12180
catttataac actcctatttt tttatgtttt gctaccccatt catattcacg atgttttgta  12240
tcagcgttca cattactgaa aaactctttta tattctgata tgttagcttc taatgtttgt  12300
```

```
ctcacttctc caactgcgtt accacttgac acacgtaacc atgcaccaac acgttttatt    12360
tcttccggtg cgtctttgaa taattccatt tggttgcctg taatataata ttctccgggt    12420
gttgtaacgt aagctatcca attattatat ttacttgctt ctaaatattc ttgatatggt    12480
gcgtctgttt tgattgttgt ccataaacca taatcccatt ttaacgtgaa tacatctagc    12540
gtcataccac gcataacttt taccatttta cgaccagttg aaaaacgtgt taattcttga    12600
acagtaccta atgtttgtgt tgtagggtat acattaatga aacaaccagc gtcaataatt    12660
ttttacttc catttgtagg catgttttta agcttttctg ccgtactacc gtcaatataa    12720
taaaatccag cttgcgttaa gtcatttaag tcgtcgatat ggtcaggtat agataatgca    12780
cgaccgtcat cttttgttaa tttataattt tgagaacctc ttgcacgtaa tgcttcaaaa    12840
tgttcatatt ctccaagttg gaagaaaccg tataagttat ggaatcgttt accaccaccg    12900
ccattagtca ttgcaagtaa taacgattta cgttttgttt ttgggtttgt ataaatacaa    12960
ataccctcag gctctttaaa attatcacgt gggaagttaa ttccgtcttg gtaagataac    13020
ttaaacgggt aatcgtataa cttttgacca gttgttaatg aatctttgcc aatttgcaca    13080
tgtgaattaa ctgaactgtt accacttaac cagtacaaat catcaccatc aacagcaata    13140
ccttgcatcc aacgtgcatc gttattttct gaattatcaa ttgtcatttc ttttctaca    13200
ttatcaatat gattttttaac atcagctctt gaacgtacct gtatcgtacc atcaccgaaa    13260
cgtaatacga gtttgtcatt tgcttcatca attaacggtg taaagaatg tttgtttaaa    13320
agtgactgtg gtgtataatc tgttaaccct tggcttctt ctaaatctaa tacatagtta    13380
tctttatatg ctacttgcaa cagttttgca acaccatcgt gatgtaacca tattttcatt    13440
tccccgtttg attgtctttc taatccgatt gttgtaccgt gaccaccttg tacaatacgc    13500
atactagaaa ttaaatcacc actaggcgtt aattattaa tccaaaatcc ctcaggtgtt     13560
tgtgagtcgg attgtgttga gtacattga ttcgtttctt tatcaatatt aatagattgg    13620
ttcacagcgt tacgaatacc cccaaagccc attacaaact taggttcaag ctcatttaat   13680
tcgaacccat taacaaaacg gttaatgtct ttaattaagt ctttaacttc tgctttaaaa    13740
tcattcattt gtttcatttc agcaacttta aataatgcaa atgcagatgt aagaccggca    13800
ctatatttag taaattcatc atgaataatg ttatctatcg taccatcatt taaccaacct   13860
ctaaataatt ctttagcttg gtctgggaat gctttcatta agtcgtccca atttttgaaa    13920
cgttttttta actcatcgtc atagtcccaa atacgatgtg ctaatacttc aatgagcttt   13980
gataatcttg aaatataatc ataatatgat tttgaattgg tattataatc tgctctatca   14040
tcgtaaaacg gtgtataacg ttctctcgtt ttatatattt cgtctaaaaa tggacgaatg   14100
tcgtcaaaat atttaaaatc gttttcatta tatgccataa ttttccacct ttaccaaatt    14160
tgtaaaaaac atttttttat caaattcatt taaaattttc tttcttaaat cgtatacttt    14220
atcaatatta tcaattaaat actgttttga aaattgtgtg cctttcgcat taccttttg    14280
attttgatta cgttttacgt tttgattact ttcgttactt gatttattca cagttttacc   14340
gttatcaatc gtgttattgt ctgcaaattt taacgttgtt ttatctacat caatgttaac   14400
ctcgctttgt ggtaatgaca cataagcatt tctgttcgct gtcataccag ttgaattgtc    14460
taaagatgta gcattttgat ttgatgtttc atctgtgttg tttgttgtat cttcattatg   14520
ttctgtaaaa ccttgtgatt gtagatattt ttcaacttca cttgatgaat aaacaacatt    14580
caaataatcc tcatgtgtga tacatacagt aatcacttgc ataccaaatg cctcaactgt    14640
ttgtctgtta atctctctat ctaaaaaatg aatcgtaaat gattttttaa aaagtaagtc    14700
```

-continued

```
tgataaatct tctttcaatg aaaaacctt  aaatactttt tcattaacga tagctaaaac   14760
atctttatcg aatttcaaca ttttttgcat aaattgaaaa tcatcatcat aaaacgttaa   14820
tttattatca tttacaaatt cattgaaacc tttttaata agctcagatt taataaaatc   14880
gtataaagtc attgtatatc tagccattta aatcactact ttcatctttt aaaagtgtgt   14940
caaccattga tattttagac gttgtttcat catcgtaata cggtttaata tctaaaccat   15000
agcgtttaga taaaaacgtg attggttcac gacctttaa ataaatatta ctatttgatg   15060
ttgtaaaacc acgattactt ttagcttctt catctgatac accactttct ttatcaacag   15120
ctaaagagtt aatacctaaa tagttactta attcactaat cttattttga tactctcttt   15180
tcatctcagt taaagcagga atcacactat tacttgttaa atcaataatg tcatcttctg   15240
cattaaacat aggtgacatt ttaacaaatg gtgcaccgtt atatatttct gatacaagtt   15300
gattaattga ctcgtcatta atttctgatt taaatacctt gctaaatttc gcttgcataa   15360
tcaatgaaaa tcgagataaa acaacttcag ctaattcatc ggtatagtgt tcaatgattt   15420
caatatcact attatactgt ataggtttat tttgcataac aacaaagtta ccactcatac   15480
aattatcgta tagcttatga atttgtagac actcatcagg aattaaatag tcaggtacaa   15540
taaaataaat atcttctttt gttaatcgtt tttgaaattg gaaattaaag tttgatgaaa   15600
aatttggtgc ttgattaaaa taggtattat ttacataacc aagtatcata atttgtttat   15660
ttctagcttc accaaccact acattaatat tttgccttaa tgcagactct aactgtataa   15720
aatctatacc aaccgtatca cgattggtat agtttataag tagggtaaa aattccaaat   15780 aacgattaaa cataagacgt ttaaatctgt tgcgatgttc aacaactctt ttgttgattt   15840
cttttgataa ttcaacgttt aaacctcttt tatcgttgtt catatttacg ctcctttat   15900 tctgttgctt cttcctctag ttttggtgtt acatcttggt cagtaattaa tattttatta   15960
aagaatggac taatagcctt gaatgaataa taatgaatcc agtgtgtgac ctcatcaaat   16020
tcaccattat agaatggttg ttttaacata cctttggtat aacgtttgta tttaattgca   16080
ttaatatcta aaataaatgc gtataaatct gattttggtt taatttcttc aatgttacca   16140
gtaaactctt taagttaga aacatcataa gtaaatactg caccaactgg aattgtgtca   16200
ccaatttgcg actgataatc accgtaagca cgtaagaaat caattgtctc ttgattttgt   16260
aatttaaatt cttttgttac tttaaacaca ccacctaaat catcaaaact tataacatgg   16320
tctgtaaaat caataccagc gatttggaat gtgttagcaa ttttgtatc taataggtaa   16380 gattttaaag aatctgttgt taaaataaca atatctttta acttagatac agttgtatat   16440
tgaccaattg caccaccaga agcacggtga acttcattgt atttagcgct gttgttttgt   16500
aagtttaaaa ttgcttcaaa tactttgctt gctaaatctt cttttgatgt tgttttacgt   16560
acgtttgact ctgataattg atttaatgag taatcaacta acattgctcg catttctttt   16620
tcttctaata cattaatatc agaaattttc ttttatata cacctaatgc gtaatttgtt   16680
gcgtctgcta atgtttggaa attgaaacgt gtatcattat tgtttaatgt gaattttgt    16740 ttcttcacaa taccactacc atataactta gtagccatac gtggataatt acgtttcaac   16800
attaattcct cattttttga taaatccata ttaattggta ctgtatccat aatgacatat   16860
tcttcactat attgaccaat aaagtcttgt tctttagcta accaattaaa acggttacct   16920
aaagcaatat caattaataa tgtctcgtta atcttaggga ataaatattt atttacaaat   16980
gtttcaaaca ttgtattatt gttatcccat ttatcaccaa atgtccaaga ttttgaataa   17040
tcatggttaa aatcttgtaa tgccgacttt gcagattttg ctactaaaag agctgtttcg   17100
```

-continued

```
tttttttgtac ttgctggtgc cataatttat tattcctcct ctacgtctcc gctaaaagtt    17160
tgttttgaaa gtgaatggat ttgtacaccg tactcatctt cacttttgtt tacatctatt    17220
gacatatttt catttaattc agtacgttta tttaaacgtg aatcttcata tgatgtcccc    17280
atcatagaac gcatgttatt gccttcatac atattatttt cctcctaatc taaatctaac    17340
ttgtcaacta attcttcatc tgaatagtct ttatcttctt tgtcagcatt tgttacatct    17400
ggttgtgttt gttgtggttg ttgaatttgt gatgataaaa aagtagtcat ttgttgctct    17460
aatgatgtaa tacgttgttc taatataaca gggtcgaatt ttgaactatc ttcatctgtt    17520
atagtaggtt ctaatttatt cttattttct tcttcaattg tttctactgt tttatcttca    17580
gtaggttctt cagttggttc ttcagttggt tcttcagttg gttctttgtc gtctggtttt    17640
acgatttcct caaattctgt cattgtgaca cctccaaaat attttataac taattatatc    17700
atagaatatt taaataagta aattaaattt attaaaaagc gtgaacatag ttttcaataa    17760
aagtaaatag atgtatatat tttgtaatta atgaatatgt aataggttag ataagttgga    17820
aaagtaggtg aacatttttt ataagtttag tttagaaatg ataagttaat ttataagttt    17880
tgatttgtat aatcgtttat tttaaacggt ggggaggtgt aaatttacaa aaacttttt     17938
```

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 2
taatacgact cactataggg cga                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 3
gtattctata gtgtcaccta aat                                              23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 4
cgtaatgctt caaaatgttc                                                  20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 5
gagcaatgtt agttgattac tcatt                                            25
```

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 6
ccatttaaaa aataatcatc acgtt                                               25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 7
tgcaattcat atattagatg ataa                                                24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 8
tatgctttat atggaggttg ataac                                               25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
aattagtgta ccgtcaccta aaga                                                24

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
tgcaacacca tcgtgatgta                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 11
gttgttgaac atcgcaacag                                                     20
```

```
<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 12
caaaatctga taaaaacgtc at                                                  22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 13
gacgtgatga ggattattat                                                     20

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 14
ataaattctc tttcttttc ctcaaattca aatctcgcta atgt                           44

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 15
catacgtgga taattacgtt tcaacattaa ttcctcattt                               40

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 16
atcaaattca tttaaaattt tctttct                                             27

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 17
aatgtcacct atgtttaatg caga                                                24
```

```
<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 18
agttcatcat ttaagaattg aacaacagaa ct                                    32

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 19
tttgttgctc taatgatgta atacgttgtt ctaatataac ag                         42

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 20
tcacttgcaa taataccact ttctaat                                          27

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 21
gtcaagtatc attttaatac aattt                                            25

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 22
tcattataca ttacgtgacg ctta                                             24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 23
agcttctctt tcttttttcc atcta                                            25
```

```
<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 24
gaacttcatt gtatttagcg ctgttg                                            26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 25
tgaatcttca tatggtcgac ctgcag                                            26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 26
atttaatagt tttgcacaag taccaa                                            26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 27
caaactaacc catctgataa acaaac                                            26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 28
aacctaatgg ctattggttc caacca                                            26

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 29
ggtaacagtt cagttaattc acat                                              24
```

```
<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 30
ggtgccataa tttattattc ctcc                                           24

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 31
ttaatcgtac ctaatttaat atcac                                          25

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 32
aacgtaaatc gttattactt gcaatg                                         26

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 33
cgttacaaca cccggagaat atta                                           24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 34
ccaaatgtcc aagatttga ataa                                            24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 35
tttaaaatgt acaggtacgt atac                                           24
```

```
<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 36
ttgaatttaa cgaatataat ttggc                                          25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 37
atattatcat gattgcacat aactg                                          25

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 38
gtaaaaggtt atggacgttt taat                                           24

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 39
aatttttatg actatataaa atcatt                                         26

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 40
acaaaaaaca tttaacaaca cgtat                                          25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 41
aaataaaata caaacataa tcaat                                           25
```